United States Patent [19]
Morgan et al.

[11] Patent Number: 5,593,426
[45] Date of Patent: Jan. 14, 1997

[54] DEFIBRILLATOR SYSTEM USING MULTIPLE EXTERNAL DEFIBRILLATORS AND A COMMUNICATIONS NETWORK

[75] Inventors: Carlton B. Morgan; Daniel Powers, both of Bainbridge Island; Clinton Cole, Seattle; Steven T. Mydynski, Bothell, all of Wash.; Michael J. Leventhal, Palo Alto, Calif.

[73] Assignee: Heartstream, Inc., Seattle, Wash.

[21] Appl. No.: 351,654

[22] Filed: Dec. 7, 1994

[51] Int. Cl.⁶ .................................................. A61N 1/39
[52] U.S. Cl. ................................................ 607/5; 128/903
[58] Field of Search ................................. 607/5, 32, 60; 128/695, 696, 903

[56] References Cited

U.S. PATENT DOCUMENTS

| | | | |
|---|---|---|---|
| 3,724,455 | 4/1973 | Unger | 607/5 |
| 4,102,332 | 7/1978 | Gessman | 607/5 |
| 4,531,527 | 7/1985 | Reinhold, Jr. et al. | 128/696 |
| 4,635,639 | 1/1987 | Hakala et al. | 128/696 |
| 4,928,690 | 5/1990 | Heilman et al. | 128/696 |
| 5,078,134 | 1/1992 | Heilman et al. | 128/696 |
| 5,181,519 | 1/1993 | Bible | 128/704 |
| 5,228,449 | 7/1993 | Christ et al. | 128/691 |
| 5,300,093 | 4/1994 | Koestner et al. | 607/32 |
| 5,336,245 | 8/1994 | Adams Theodore et al. | 607/32 |
| 5,348,008 | 9/1994 | Bornn et al. | 128/696 |
| 5,416,695 | 5/1995 | Stutman et al. | 364/413.02 |
| 5,417,222 | 5/1995 | Dempsey et al. | 128/696 |
| 5,440,449 | 8/1995 | Scheer | 361/686 |

FOREIGN PATENT DOCUMENTS

| | | | |
|---|---|---|---|
| 0167122B1 | 1/1986 | European Pat. Off. | A61N 1/39 |
| 0409591A1 | 1/1991 | European Pat. Off. | A61B 5/0428 |
| WO94/00182A2 | 1/1994 | WIPO | A61N 1/39 |

OTHER PUBLICATIONS

Cummins, et al., "Improving Survival from Sudden Cardiac Arrest: The 'Chain of Survival' Concept," *Circulation* (May 1991) 83:1832–47.

Ornato, "The Earliest Thrombolytic Treatment of Acute Myocardial Infarction: Ambulance or Emergency Department?" *Clin. Cardiol.* (Aug. 1990) 13:27–31.

*Primary Examiner*—George Manuel
*Assistant Examiner*—Carl H. Layno
*Attorney, Agent, or Firm*— Morrison & Foerster

[57] ABSTRACT

A defibrillator system comprising an external defibrillator, a defibrillator communicator and a communication network. In a preferred embodiment, the defibrillator comprises electrodes, an energy source and a controller, with the controller comprising an ECG signal analyzer and local actuator on the defibrillator for delivering an electrical pulse from the energy source to the electrodes. The communication network comprises a communication station, preferably a computer with a modem, and signal carriers, such as telephone lines, so that information can be transmitted from the communicator to the communication station. The defibrillator communicator automatically transmits information to the communication station in response to deployment of the defibrillator. In alternative embodiments, additional information (such as patient ECG data and defibrillator operation data) is sent from the communication station to the communicator. A method of operating such a defibrillator system is included.

44 Claims, 2 Drawing Sheets

DEFIBRILLATOR SYSTEM USING MULTIPLE EXTERNAL DEFIBRILLATORS AND A COMMUNICATIONS NETWORK

BACKGROUND OF THE INVENTION

This invention relates to defibrillators, particularly semi-automatic and automatic external defibrillators, and communication networks for transferring information to and from defibrillators on the networks. The invention also relates to methods of operating and maintaining defibrillators in communication networks.

One frequent consequence of heart attacks is the development of cardiac arrest associated with a heart arrhythmia, such as ventricular fibrillation. Ventricular fibrillation may be treated by applying an electric shock to the patient's heart through the use of a defibrillator. Cardiopulmonary resuscitation (CPR) is commonly used to treat victims of cardiac arrest until a defibrillator can be brought to bear on the victim's arrhythmia.

The chances of surviving a cardiac arrest decrease with time after the attack. Quick response to an arrest by performing CPR and/or by administering a defibrillating shock is therefore of critical importance. The American Heart Association's "Chain of Survival" recites the following steps:

1. Rapid access to medical care, such as by activating an emergency response system (e.g., calling an ambulance);
2. Rapid CPR initiated by a bystander or other early caregiver to help the victim survive until more advanced care arrives;
3. Rapid defibrillation; and
4. Rapid application of Advanced Cardiac Life Support (ACLS), such as airway management, drugs, etc. The benefits of this approach are discussed in more detail in Cummins, et al., "Improving Survival From Sudden Cardiac Arrest: The 'Chain of Survival' Concept," 83 *Circulation* 1832–47 (May 1991).

Physicians have suggested keeping a cellular telephone, radio or other communication device with defibrillators so that medical help can be summoned near the time that treatment for a heart attack begins. The prior art has attempted to address this need by providing patient monitors and defibrillators that have some communication features so that medical help can be sought more quickly. For example, Reinhold, Jr. et al. U.S. Pat. No. 4,531,527 describes a cardiac monitoring system in which patient units mounted on patients collect and analyze patient ECG information. The patient units thereafter transmit the collected and analyzed information telephonically to a remote office unit. The office unit can then transmit the information to a physician.

Christ et al. U.S. Pat. No. 5,228,449 describes a system for detecting out-of-hospital cardiac emergencies and summoning emergency assistance. A wrist-mounted monitor detects a patient's pulse through use of infrared photoplethysmography and sends RF signals to a base unit. If the patient suffers a cardiac arrest, an alarm will sound in both the wrist unit and the base unit. The base unit will automatically connect to a telephone line to dial for assistance. The device also has a removable instructions player that provides CPR instructions to anyone assisting the heart attack victim.

Gessman U.S. Pat. No. 4,102,332 describes a portable defibrillator with a pre-programmed dialer that telephones a physician when activated by the user, i.e., the patient or attending caregiver. While the physician and the patient and/or attending caregiver communicate with each other via the defibrillator's communication system, the physician alone controls operation of the defibrillator from his or her remote location. During use, the defibrillator sends operation and status data to the physician.

Adams et al. U.S. Pat. No. 5,336,245 describes an interrogator for an implanted defibrillator. The interrogator communicates with the implanted defibrillator via RF signals. The interrogator communicates with a nearby modem via RF, IR, or over a hard wire. The modem, in turn, sends defibrillator data via telephone lines to a physician's office. The physician can also control operation of the interrogator remotely and can send information to the patient for display on the interrogator display.

Heilman U.S. Pat. No. 5,078,134 describes an automatic external defibrillator mounted in a belt on a patient. The defibrillator transmits patient data via RF with a separate "maintenance unit." The maintenance unit communicates telephonically with a physician via a modem, dialer and speakerphone when a user depresses a button to dial the physician.

The disclosures of the patents cited above are incorporated herein by reference.

SUMMARY OF THE INVENTION

This invention provides a defibrillator system comprising an external defibrillator, a defibrillator communicator and a communication network. In a preferred embodiment, the defibrillator comprises electrodes, an energy source and a controller, with the controller comprising an ECG signal analyzer and means for local actuation of the defibrillator to deliver an electrical pulse from the energy source to the electrodes. The communication network comprises a communication station, preferably a computer with a modem, and signal carriers, such as telephone lines, so that information can be transmitted from the communicator to the communication station. Likewise, the defibrillator communicator comprises means for automatically transmitting information to the communication station in response to deployment of the defibrillator.

In alternative embodiments, additional information (such as patient ECG data and defibrillator operation data) is sent from the communicator to the communication station, and information (such as use instructions) is sent from the communication station to the communicator.

The invention also includes a method of operating such a defibrillator system.

The invention is explained in more detail below with reference to the drawings.

DETAILED DESCRIPTION OF THE PREFERRED EMBODIMENT

Figure 1:
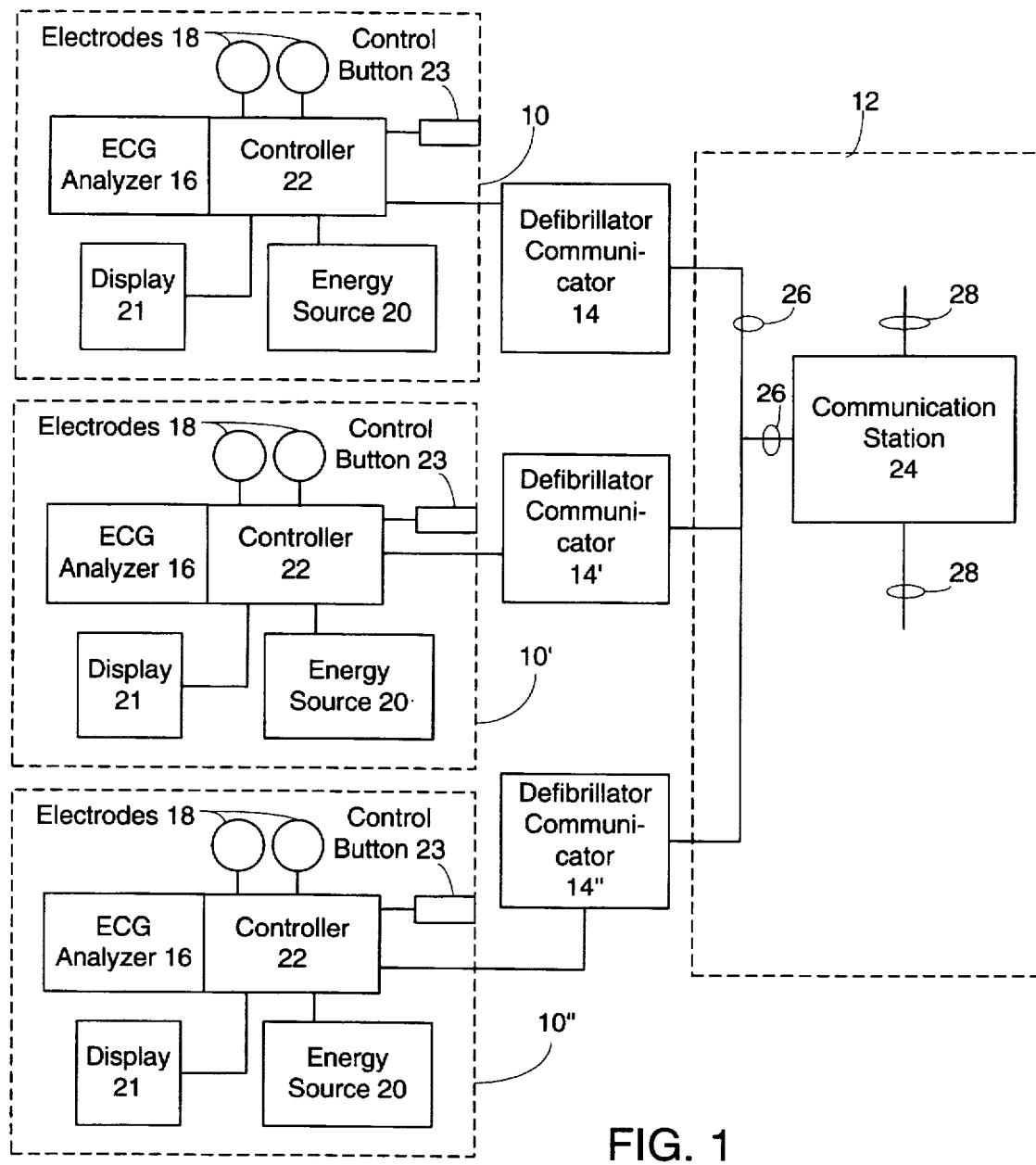
FIG. 1 is a schematic block diagram illustrating a defibrillator system according to a preferred embodiment of this invention.

FIG. 1 is a schematic block drawing illustrating a defibrillator system according to a preferred embodiment of this invention. A defibrillator 10 is associated with a defibrillator communicator 14, which communicates with a communication network 12. The defibrillator is preferably a semi-automatic external defibrillator. Its primary components are an ECG analyzer 16 for receiving patient ECG information from a patient through electrodes 18; an energy source 20 to deliver a defibrillation shock to the patient through electrodes 18; and a controller 22 controlling the operation and analysis of ECG analyzer 16 and the delivery of the defibrillation shock after local actuation by an operator. The local actuation can be initiated by activating a control button 23 or other defibrillator operator user interface (such as a knob, wheel, switch, etc.) to send an actuation signal to the controllers preferably in response to a shock recommendation shown on defibrillator display 21. Alternatively, the defibrillator may be an automatic external defibrillator, in which case the defibrillator is self-actuated, i.e., the defibrillator generates an actuation signal and delivers a shock to the patient automatically solely in response to the ECG analysis.

Many features of the defibrillator may be made according to the defibrillators described in copending U.S. patent application Ser. No. 08/227,553, "Electrotherapy Method and Apparatus," filed Apr. 14, 1994, and in copending U.S. patent application Ser. No. 08/240,272, "Defibrillator With Self-Test Features," filed May 10, 1994. The disclosures of these patent applications are incorporated herein by reference.

The primary components of the communication network 12 are a communication station 24 and the signal carriers 26 linking the defibrillator communicator 14 with the communication station 24. The communication station 24 may include, e.g., a computer located at a remote site, such as an emergency medical care facility or a medical response dispatch center. Alternatively, the communication station may include some other microprocessor-controlled data collection and sending device.

In the preferred embodiment, the communication network is a telephone network. The signal carriers 26 may therefore be telephone lines, RF signal carriers (for cellular telephone communication), or a combination thereof. Defibrillator communicator 14 therefore includes a telephone modem for sending and/or receiving data from the telephone lines and possibly a cellular telephone link (not shown). Communication station 24 would also include a modem for sending and/or receiving data to and from the defibrillator communicator via the telephone lines. Standard telephone voice connections may be provided on the communicator and on the communication station to permit voice communication, as discussed further below.

Additional signal carriers 28 may be provided to link the communication station 24 to other communication stations on the communication network or to other network elements. In addition, a plurality of other defibrillators, shown as elements 10' and 10", may be connected to the communication network as well through their respective defibrillator communicators 14' and 14".

In an alternative embodiment, the defibrillator communicator 14 is actually part of the defibrillator itself and not a separate component.

A preferred method of operating the defibrillator system of this invention is as follows. In the event of a cardiac emergency, the first responding caregiver initiates deployment of the defibrillator. The initial step of deploying the defibrillator is a triggering event that establishes a communication link between the defibrillator communicator 14 and the communication station 24 at an emergency medical care facility. Information thereafter begins to flow between the defibrillator communicator and the communication station. The information sent by the defibrillator communicator preferably includes at least (1) the fact that the defibrillator has been deployed and (2) defibrillator identification information. Alternatively, the triggering event could be the activation of a switch or other actuator by a user to establish a communication link.

In the preferred embodiment, the defibrillator also sends information like patient ECG data, defibrillator operation condition data, defibrillator maintenance data, signal artifact data, etc., to the defibrillator communicator. The defibrillator communicator sends this information to the communication network. Other information, such as defibrillator location information (for use by the ambulance or other emergency medical responder), user voice, and defibrillator/communicator identification information may be supplied by either the defibrillator or the communicator and sent to the communication network by the communicator.

The communication network may simply receive the deployment, identification, and any other information from the communicator. In the preferred embodiment, however, a network communication station sends information to the communicator and/or defibrillator. This information includes CPR instructions, defibrillator use instructions (for use by the caregiver) and other audio and visual information.

If the user decides to attempt defibrillation, the defibrillator electrodes are placed on the patient and the defibrillator is activated. The defibrillator's ECG analyzer receives and analyzes ECG information from the patient. If the ECG information indicates that a defibrillation shock is needed, the defibrillator either (1) advises the user to administer a shock (if the defibrillator is semi-automatic) so that the user can decide whether or not to actually deliver a shock or (2) automatically administers the shock to the patient through the electrodes.

Figure 2:
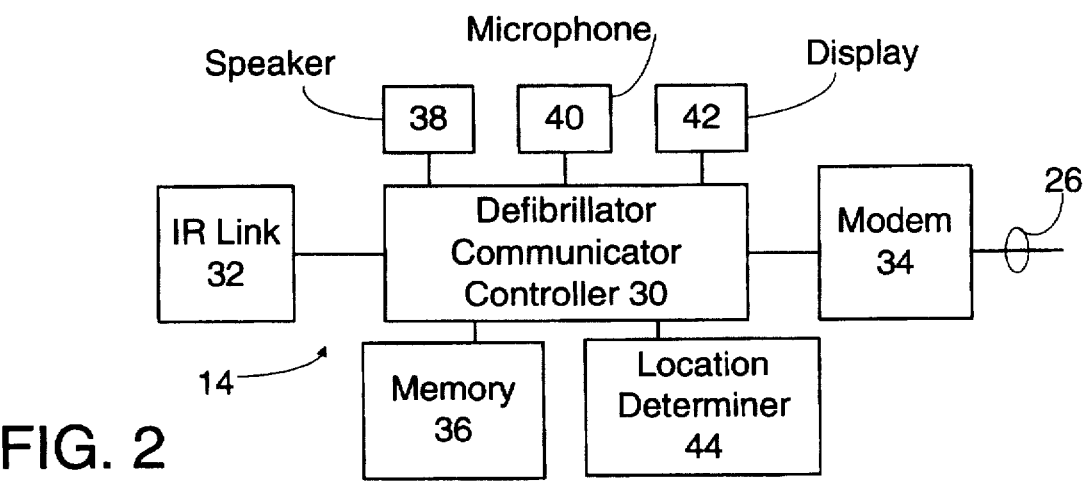
FIG. 2 is a schematic block diagram illustrating the components of a defibrillator communicator according to one embodiment of this invention.

FIG. 2 shows an embodiment of the defibrillator communicator in which information passes between the defibrillator and the communicator. In this embodiment, defibrillator communicator 14 is separate from its defibrillator (not shown). Communication between the defibrillator and defibrillator communicator 14 is via infrared signals, in a manner known in the art. Defibrillator communicator therefore has an IR link 32 for sending infrared signals to, and receiving infrared signals from, a defibrillator, which has a corresponding IR link of its own. IR link 32 is controlled by a defibrillator communicator controller 30.

In this embodiment, the communication network is a telephone communication network. Defibrillator communicator 14 therefore has a modem 34 controlled by controller 30 for transmitting data streams to, and receiving data streams from, telephone line 26 of the communication network. Voice communication is sent on line 26 in a separate analog channel.

The defibrillator communicator 14 of this embodiment has additional user interface elements. A speaker 38 broadcasts use instructions or other information received by the communicator 14 from the communication network or derived from the communicator memory 36. A microphone 40 receives sound information from the user or patient for storage in memory 36 and/or transmission to the communication network. The communicator also has a visual display for displaying text, still pictures or video instructions and other information. As with the other information, this displayed information may come from communicator memory 36 or from the communication network via modem 34.

The defibrillator communicator passes information between the defibrillator and the communication network continuously, periodically or on demand, depending on the use state of the defibrillator. For example, when the defibrillator is not being used, the defibrillator may send maintenance, calibration, expiration date and/or self-test information to a communication station on the communication network via the defibrillator IR link (not shown), defibrillator communicator IR link 32 and modem 34. Examples of defibrillator maintenance and calibration information can be found in U.S. patent application Ser. No. 08/240,272, referred to above. Such information could include movement of a defibrillator operation parameter (e.g., battery voltage) outside of a predetermined range and expiration of a preset operation period of a defibrillator component (e.g., expiration of the useful life of the electrodes stored with the defibrillator).

This information may be sent periodically on a schedule controlled by the defibrillator or upon a request sent from the communication station on the communication network. The network's communication station can use this information to determine whether to remove the defibrillator from service, which may be done remotely by sending a suitable signal from the communication station to the defibrillator through the defibrillator communicator. A defibrillator may also be removed from service for other reasons, such as (1) if the defibrillator is moved outside a prescribed region, (2) if contact between the defibrillator and the communication network is not established within a preset time, or (3) if a local environmental parameter (such as temperature) moves outside of a preset range. This feature helps prevent lost, stolen or possibly damaged defibrillators from being used improperly.

The defibrillator can be maintained locally, of course, without communicating with the communication network, through manual maintenance or self-maintenance. The ability to communicate with a communication station, however, enhances the defibrillator's maintenance capabilities.

During use of the defibrillator, the defibrillator can send patient ECG information to the communication station through the defibrillator communicator. The defibrillator can also send defibrillator operation information (such as capacitor charge status, electrode voltage and current measurements, and signal artifact data) to the communication station through the defibrillator communicator. Additional information can be gathered by the microphone 40 on the defibrillator communicator, such as verbal descriptions of the patient's condition. This information is useful to medical personnel in developing a treatment approach for the patient.

Information may also be sent from the communication station on the communication network to the defibrillator communicator and defibrillator while the defibrillator is in use. This information includes defibrillator use instructions which may be broadcast on the communicator's speaker 38 and/or displayed on the communicator's display 42. In an alternative embodiment, the communication station may also send defibrillator control signals to remotely control the operation of the defibrillator. In the preferred embodiment, however, the defibrillator is actuated locally, either automatically or semi-automatically in response to its analysis of the patient's ECG signals and does not need to receive any information or control signals from the communication network in order to treat the patient. Thus, when the communications link is for some reason not available, the defibrillator can be used autonomously to treat the patient effectively. When the communication system is available, the ability to treat the patient is enhanced.

One particularly useful aspect of this invention is the ability to use one communication station to interface with multiple defibrillators on the communication network. Thus, for example, each of the defibrillators 10, 10' and 10" shown schematically in FIG. 1 could send and receive information to and from the communication station 24 in the manner described above.

The information flow between a defibrillator and a communication station does not need to occur in real time. Information from the defibrillator can be temporarily stored in defibrillator communicator memory 36 before being transmitted to the communication network, and information or control signals from the communication network can be stored temporarily in memory 36 before being transmitted to the defibrillator. Information may thus be transmitted without the aid of a user.

One optional additional feature of the defibrillator system of this invention is a location determiner 44 in the defibrillator communicator. Location determiner 44 sends location information to the communication station on the communication network so that medical personnel responding to a request to assist the patient will be able to find the patient. Location determiner 44 may be simply location information stored in defibrillator communicator memory and sent to the communication station by the defibrillator communicator. Alternatively, the location determiner might incorporate a satellite-based global positioning system (GPS) in a manner known in the art.

As mentioned above, in an alternative embodiment each of the defibrillator communicator features discussed above could be incorporated into the defibrillator itself, thereby making the defibrillator communicator simply another part of the defibrillator instead of a separately identifiable component of the system.

One important aspect of this invention is the ability to automatically notify medical personnel that the defibrillator may be needed to treat a patient. Any step in the use of the defibrillator may be used as a triggering event to send a message to the communication network's communication station that someone intends to use the defibrillator to treat a patient. The triggering event may be, for example, removal of the defibrillator from a holder or turning on the defibrillator's power switch. This feature makes deployment of the defibrillator simultaneous with dispatch of emergency medical personnel.

Figure 3:
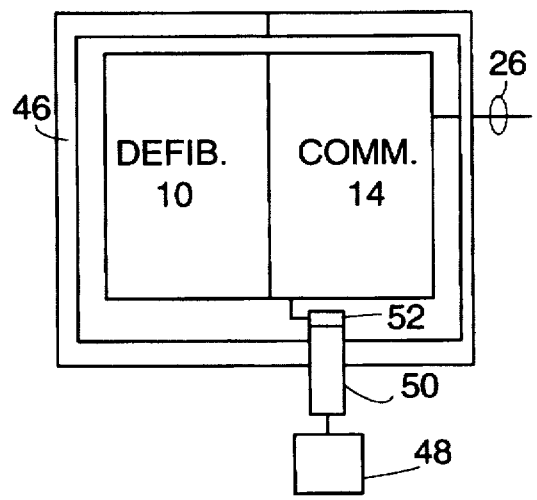
FIG. 3 shows an optional lock and lock actuator as part of the defibrillator system of this invention.

FIG. 3 shows one example of an implementation of this notification feature. In this example, the defibrillator and defibrillator communicator are disposed in a locked holder 46. To request use of the defibrillator 10, the user must activate a use requester 48 on the holder 46. Use requester 48 may be, e.g., a button, lever, or switch. Activation of the use requester 48 is a triggering event that sends a signal to the communication station on the communication network through defibrillator communicator 14. In response, the communication station (1) sends a return signal to the defibrillator communicator authorizing the operation of a lock actuator 52 to open lock 50 so that the user can access the defibrillator; (2) dispatches emergency medical personnel to the defibrillator's location; and (3) begins sending any required use information or control signals to the defibrillator.

Figure 4:
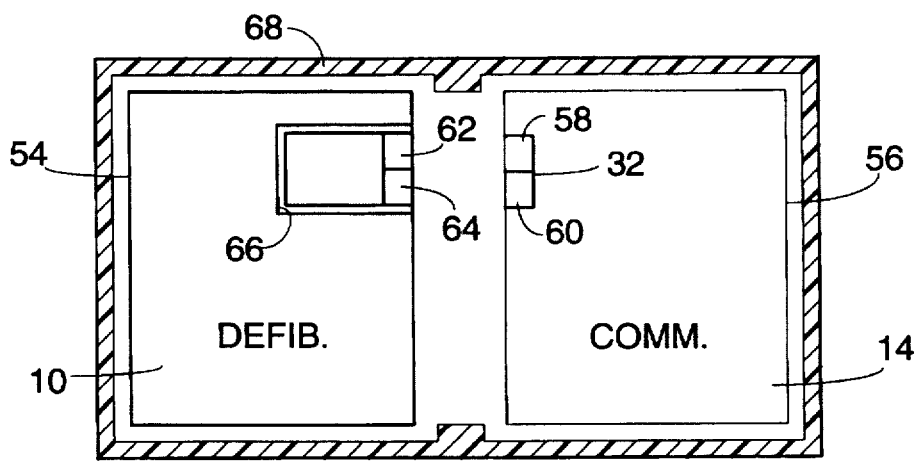
FIG. 4 shows an embodiment in which the defibrillator and defibrillator communicator of this invention are mounted in a holder.

FIG. 4 shows one possible arrangement for the defibrillator and defibrillator communicator of this invention. Defibrillator 10 and defibrillator communicator 14 are each disposed in separate housings 54 and 56, respectively. As discussed above, defibrillator communicator has an IR link 32 which includes an infrared transmitter 58 and an infrared receiver 60. Defibrillator 10 also has an IR link which includes an infrared receiver 62 and an infrared transmitter 64. The defibrillator IR link may optionally be disposed in a PCMCIA format slot 66 in the defibrillator in a manner known in the art. The housings 54 and 56 are disposed in a holder 68 so that defibrillator infrared transmitter 64 is aligned with defibrillator communicator infrared receiver 60 and defibrillator infrared receiver 62 is aligned with defibrillator communicator infrared transmitter 58.

The common holder 68 may be used even if no information is transmitted between the defibrillator and defibrillator communicator, of course.

The communication features of the defibrillator system of this invention may be used in non-emergency situations. For example, defibrillator use training and certification sessions may be conducted from remote sites. The instructor (either human or a computer) can control a "training mode" from a communication station on the communication network by presenting training scenarios and practical examinations to users at remote sites. A user may also contact an instructor at a communication station to seek help or guidance in non-emergency situations.

The defibrillator system of this invention can also be used to communicate with a central database or registry to (1) record device tracking information pursuant to FDA regulations; (2) compile device maintenance or use statistics for reliability assessments; (3) gather medical research information; (4) evaluate training levels of multiple, diversely located users. The defibrillator system can also be used to order supplies from a central supplier.

Finally, the defibrillator system of this invention can be used to transmit use instructions from a communication station for local storage in a defibrillator. In this way use instructions can be updated as use protocols change.

Other modifications will be apparent to those skilled in the art.

What is claimed is:

1. A defibrillator system comprising an external defibrillator, a defibrillator communicator and a communication network, the defibrillator comprising electrodes, an energy source and a controller, the controller comprising an ECG signal analyzer and means for local actuation of the defibrillator to deliver an electrical pulse from the energy source to the electrodes;

the communication network comprising a communication station and signal carriers, the communication station comprising means for receiving information over the communication network from the defibrillator communicator, the defibrillator communicator comprising means for automatically transmitting information to the communication station in response to deployment of the defibrillator.

2. The defibrillator system of claim 1 wherein the defibrillator comprises means for local actuation comprising a defibrillator operator interface for operating the defibrillator to discharge a shock into a patient.

3. The defibrillator system of claim 2 wherein the means for local actuation further comprises a control button, knob, wheel or switch.

4. The defibrillator system of claim 1 wherein the means for local actuation comprises means for automatically delivering an electrical pulse from the energy source to the electrodes solely in response to an ECG analysis.

5. The defibrillator system of claim 1 wherein the communication station further comprises means for transmitting information to the defibrillator communicator and the defibrillator communicator further comprises means for receiving information from the communication station.

6. The defibrillator system of claim 1 wherein the defibrillator further comprises means for transmitting information from the defibrillator to the defibrillator communicator.

7. The defibrillator system of claim 6 wherein the defibrillator further comprises means for receiving information from the defibrillator communicator.

8. The defibrillator system of claim 7 wherein the defibrillator means for transmitting and the defibrillator means for receiving comprise an infrared transmitter and an infrared receiver, respectively, the defibrillator communicator further comprising an infrared transmitter and an infrared receiver.

9. The defibrillator system of claim 1 wherein the communication network comprises a telephone network.

10. The defibrillator system of claim 9 wherein the signal carriers are telephone lines, RF signals carriers or a combination thereof.

11. The defibrillator system of claim 1 further comprising a locking holder in which the defibrillator is mounted.

12. The defibrillator system of claim 11 in which the locking holder comprises a lock actuator communicating with the communication station.

13. The defibrillator system of claim 1 further comprising a location determiner communicating with the communication station.

14. The defibrillator of claim 13 wherein the location determiner is part of a global positioning system.

15. The defibrillator system of claim 1 wherein the defibrillator further comprises a defibrillator housing, the defibrillator communicator being disposed outside of the defibrillator housing.

16. The defibrillator system of claim 15 further comprising a holder supporting the defibrillator and the defibrillator communicator.

17. The defibrillator system of claim 16 wherein the defibrillator further comprises a PCMCIA format slot.

18. The defibrillator system of claim 17 in which the defibrillator infrared transmitter and infrared receiver are disposed in the PCMCIA format slot.

19. The defibrillator system of claim 1 wherein the defibrillator further comprises a PCMCIA format slot.

20. The defibrillator system of claim 1 wherein the defibrillator communicator further comprises a video display.

21. The defibrillator system of claim 1 wherein the defibrillator comprises a display.

22. The defibrillator system of claim 1 further comprising a second external defibrillator and a second defibrillator communicator, the second defibrillator communicator comprising means for automatically transmitting information over the communication network to the communication station in response to deployment of the second defibrillator.

23. The defibrillator system of claim 1 wherein the defibrillator system comprises more than one defibrillator in a communication network.

24. The defibrillator system of claim 1 wherein the defibrillator further comprises means for receiving information from the defibrillator communicator.

25. In a system comprising an external defibrillator, a defibrillator communicator and a communication network, a method for operating the defibrillator comprising the following steps:

automatically establishing a communication link between the defibrillator communicator and a station on the communication network in response to deployment of the defibrillator;

applying electrodes to a patient;

monitoring ECG signals from the patient;

analyzing the ECG signals to determine whether to shock the patient; and locally generating an actuation signal to deliver a shock from the defibrillator to the patient.

26. The method of claim 25 wherein the step of establishing a link comprises the step of automatically contacting an emergency medical care center.

27. The method of claim 25 wherein the step of locally generating an actuation signal comprises the step of manually engaging an actuator on the defibrillator.

28. The method of claim 25 wherein in the step of locally generating an actuation signal, the defibrillator generates an actuation signal solely in response to the analyzing step.

29. The method of claim 25 further comprising the step of transmitting information from the station to the defibrillator communicator.

30. The method of claim 25 further comprising the step of transmitting a signal from the station to unlock the defibrillator from a locked holder.

31. The method of claim 25 further comprising the step of transmitting defibrillator use instructions from the station to the defibrillator communicator.

32. The method of claim 25 further comprising the step of transmitting information from the defibrillator communicator to the station.

33. The method of claim 32 wherein the information transmitted from the defibrillator to the station is selected from a group consisting of defibrillator deployment information, identification data, patient ECG data, defibrillator operation condition data, defibrillator maintenance data, video data, voice data, artifact data, and location data.

34. The method of claim 25 further comprising the step of transmitting a signal from the station to remove the defibrillator from service.

35. The method of claim 25 further comprising the step of transmitting information between the defibrillator and the defibrillator communicator.

36. In a system comprising a plurality of external defibrillators and a communication network, a method for maintaining the defibrillators comprising the following steps:

establishing a communication link between a station on the communication network and a first defibrillator of the plurality of external defibrillators when the first defibrillator is not being used;

transferring defibrillator status information from the first defibrillator to the station;

establishing a communication link between the station and a second defibrillator of the plurality of external defibrillators when the second defibrillator is not being used; and transferring defibrillator status information from the second defibrillator to the station.

37. The method of claim 36 wherein the establishing step comprises the step of sending a request for defibrillator status information from the station to a defibrillator.

38. The method of claim 36 further comprising the step of sending a signal from the station to a defibrillator to remove that defibrillator from service.

39. The method of claim 36 wherein the establishing step is performed according to a predetermined schedule.

40. The defibrillator system of claim 36 wherein the status information transferred is selected from the group consisting of maintenance data, calibration data, expiration data, and self-test data.

41. The method of claim 36 wherein the establishing step is performed in response to a triggering event.

42. The method of claim 41 wherein the triggering event is movement of a defibrillator operation parameter outside of a predetermined range.

43. The method of claim 41 wherein the triggering event is expiration of a preset operation period of a defibrillator component.

44. The method of claim 41 wherein the triggering event is movement of a local environmental parameter outside a preset range.

* * * * *

UNITED STATES PATENT AND TRADEMARK OFFICE
CERTIFICATE OF CORRECTION

PATENT NO. : 5,593,426

DATED : Jan. 14, 1997

INVENTOR(S) : Carlton B. Morgan, et al.

It is certified that error appears in the above-indentified patent and that said Letters Patent is hereby corrected as shown below:

In the Title, at [54], please change "Defibrillator" to —Defibrillation—.

In the Inventors, at [75], please change "Leventhal" to —Levinthal—.

Column 1, line 1, please change "Defibrillator" to —Defibrillation—.

Column 3, line 18, please change "controllers" to —controller,—.

Signed and Sealed this

Eighth Day of July, 1997

Attest:

BRUCE LEHMAN

Attesting Officer

Commissioner of Patents and Trademarks